(12) United States Patent
Tanaka et al.

(10) Patent No.: US 9,921,098 B2
(45) Date of Patent: Mar. 20, 2018

(54) OPTICAL UNIT AND ENDOSCOPE SYSTEM

(71) Applicant: OLYMPUS CORPORATION, Tokyo (JP)

(72) Inventors: Yoshinori Tanaka, Hino (JP); Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/268,553

(22) Filed: Sep. 17, 2016

(65) Prior Publication Data

US 2017/0003164 A1    Jan. 5, 2017

Related U.S. Application Data

(63) Continuation of application No. PCT/JP2015/057737, filed on Mar. 16, 2015.

(30) Foreign Application Priority Data

Mar. 20, 2014   (JP) .................................. 2014-058203

(51) Int. Cl.
  *G01J 1/04*     (2006.01)
  *G02B 23/26*    (2006.01)
  (Continued)

(52) U.S. Cl.
  CPC ......... *G01J 1/0425* (2013.01); *A61B 1/00117* (2013.01); *A61B 1/0653* (2013.01); *G01J 1/44* (2013.01); *G02B 23/26* (2013.01)

(58) Field of Classification Search
  CPC ............ G01J 1/0425; G01J 1/44; G02B 23/26
  (Continued)

(56) References Cited

U.S. PATENT DOCUMENTS 8,725,234 B2 *   5/2014   Cao .......................... A61B 5/06
                                                                 385/13
2009/0040508 A1   2/2009   Hara
  (Continued)

FOREIGN PATENT DOCUMENTS

JP    2005-49820 A    2/2005
JP    2008-134138 A   6/2008
  (Continued)

OTHER PUBLICATIONS

International Search Report dated Apr. 21, 2015 issued on PCT/JP2015/057737.
  (Continued)

*Primary Examiner* — Seung C Sohn
(74) *Attorney, Agent, or Firm* — Scully, Scott, Murphy & Presser, P.C.

(57) ABSTRACT

An optical unit includes an optical element serving as a light guide path, which includes an incident entrance, an emitter, a light coupler which is arranged in the case where a plurality of incident entrances are arranged, and which couples a primary light, and a light separator which is arranged in the case where a plurality of emitters are arranged, and which separates the primary light to each of the emitters. The optical unit further includes a detector which directly or indirectly detects a leakage light leaking outside of the light guide path from the light guide path.

13 Claims, 8 Drawing Sheets

(51) Int. Cl.
    *A61B 1/00*         (2006.01)
    *A61B 1/06*         (2006.01)
    *G01J 1/44*         (2006.01)

(58) Field of Classification Search
    USPC .......................................... 250/206; 356/73.1
    See application file for complete search history.

(56) References Cited

U.S. PATENT DOCUMENTS

2011/0245616 A1*   10/2011   Kobayashi ........... A61B 1/0653
                                                                                   600/178
2013/0345517 A1     12/2013   Morimoto et al.

FOREIGN PATENT DOCUMENTS

| | | |
|---|---|---|
| JP | 2011-255015 A | 12/2011 |
| JP | 2012-127763 A | 7/2012 |
| JP | 2013-154185 A | 8/2013 |
| JP | 2014-301 A | 1/2014 |
| WO | WO 2006/098221 A1 | 9/2006 |

OTHER PUBLICATIONS

International Preliminary Report on Patentability with the Written Opinion dated Sep. 29, 2016 received in related International Application No. PCT/JP2015/057737.
Japanese Office Action dated Sep. 19, 2017 in Japanese Patent Application No. 2014-058203.

\* cited by examiner

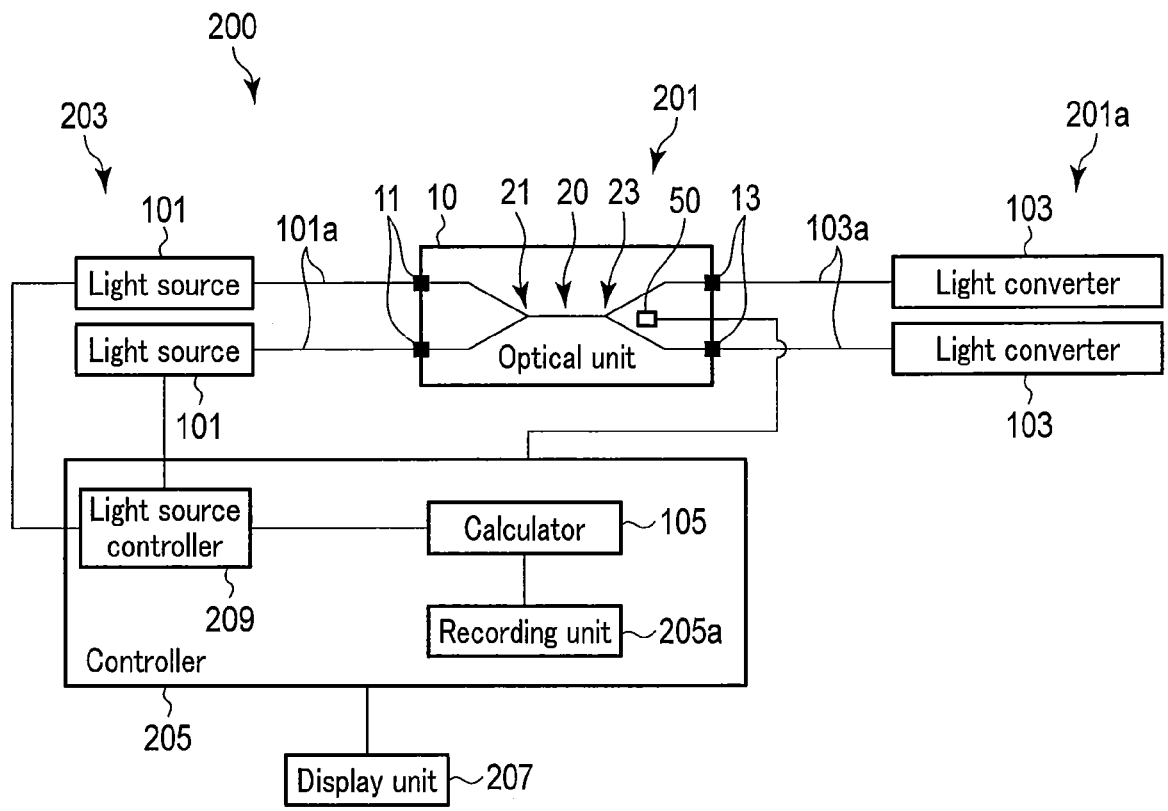
F I G. 1A
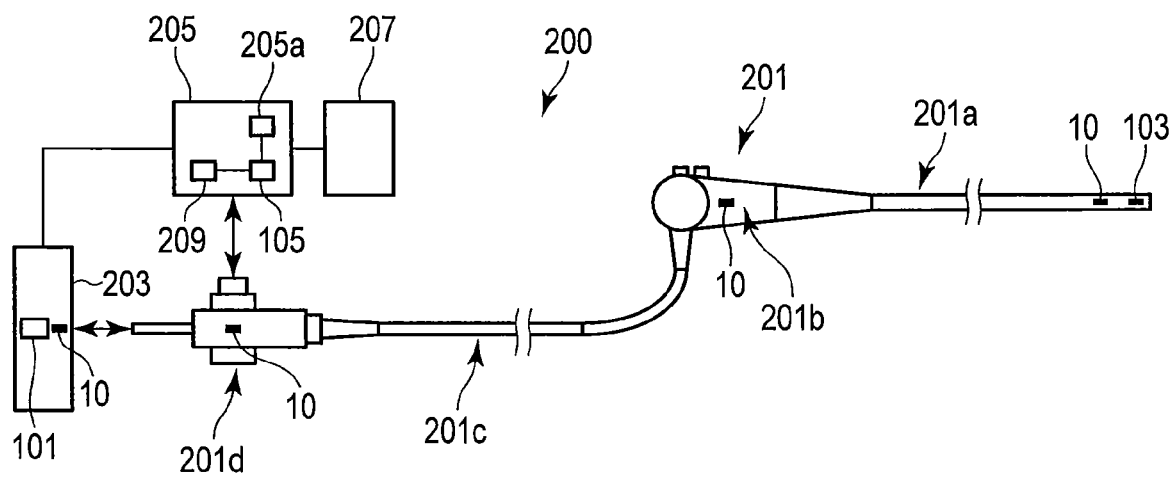
F I G. 1B

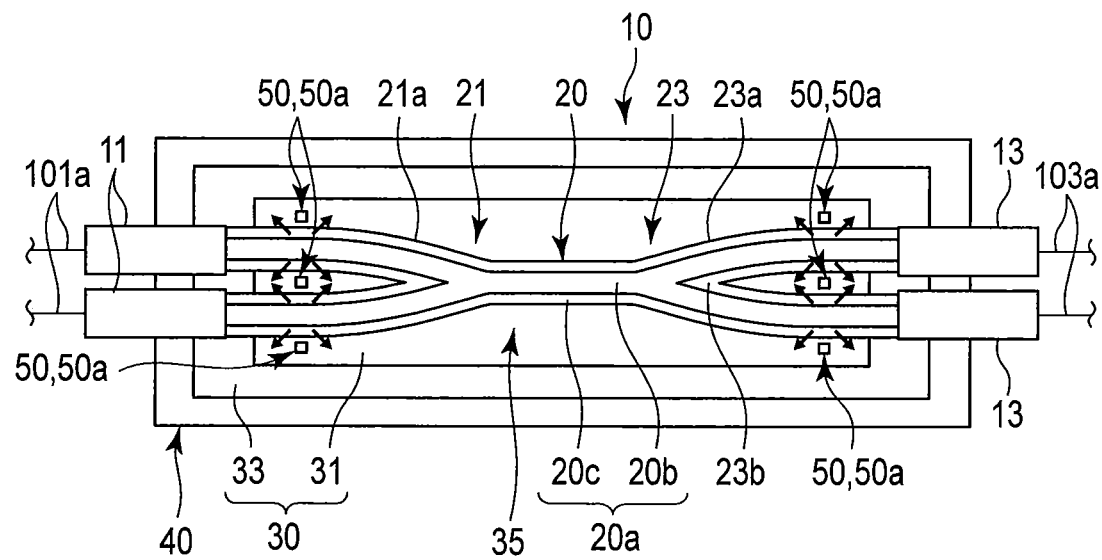
F I G. 8A
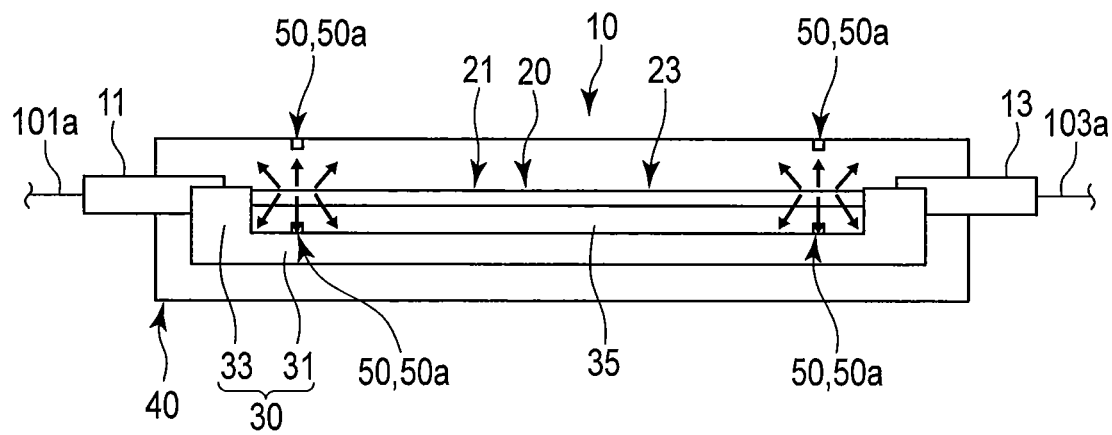
F I G. 8B

OPTICAL UNIT AND ENDOSCOPE SYSTEM

CROSS-REFERENCE TO RELATED APPLICATIONS

This application is a Continuation Application of PCT Application No. PCT/JP2015/057737, filed Mar. 16, 2015 and based upon and claiming the benefit of priority from prior Japanese Patent Application No. 2014-058203, filed Mar. 20, 2014, the entire contents of all of which are incorporated herein by reference.

BACKGROUND OF THE INVENTION

1. Field of Invention

The present invention relates to an optical unit and an endoscope system.

2. Description of Related Art

For example, in an optical connector disclosed in Jpn. Pat. Appln. KOKAI Publication No. 2005-49820, a coupler is arranged between a light source and an endoscope head portion. The coupler and the light source are connected each other by a first fiber, and the coupler and the endoscope head portion are connected each other by a second fiber. In such configuration, in order to detect the amount of light that transmits through the coupler, a third fiber connected to the coupler and a monitor connected to the third fiber to detect light intensity are further arranged.

BRIEF SUMMARY OF THE INVENTION

An aspect according to an optical unit of the invention includes one or more incident entrances into which a primary light emitted from a light source enters, and one or more emitters from which the primary light entered from the incident entrance and guided by the optical unit is emitted, wherein at least one of the incident entrances and the emitters are arranged in a plurality of numbers, the optical unit includes: an optical element including the incident entrance, the emitter, a light coupler which is arranged in a case where a plurality of incident entrances are arranged, and which couples each of the primary lights entering from each of the incident entrances in a manner that each of the primary lights entering from each of the incident entrances is guided towards the emitter side, and a light separator which is arranged in a case where a plurality of emitters are arranged, and which separates the primary light towards each of the emitters in a manner that the primary light guided from the incident entrance side is further guided to each of the emitters, the optical element serving as a light guide path which guides the primary light from the incident entrance to the emitter via the light coupler and the light separator; and a detector which directly or indirectly detects a leakage light leaking outside of the light guide path from the light guide path, including the light coupler and the light separator between the incident entrance and the emitter, and which is arranged at a position away from the optical element.

An aspect according to an endoscope system of the invention includes a light source which emits a primary light; an optical unit according to the above; a light converter which performs light conversion on the primary light emitted from the emitter and which emits the light converted primary light outside; and a calculator which calculates a light intensity on the light guide path based on the leakage light detected by the detector of the optical unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1A is a schematic diagram of an endoscope system according to a first embodiment of the present invention.

FIG. 1B is a schematic diagram of the endoscope system showing the position where an optical unit is arranged in the endoscope system.

FIG. 8A is a diagram of an optical unit in a second modified example of the second embodiment viewed from above in a state where two incident entrances and two emitters are arranged.

FIG. 8B is a diagram of the optical unit shown in FIG. 8A viewed from the side.

DETAILED DESCRIPTION OF THE INVENTION

Figure 2A:
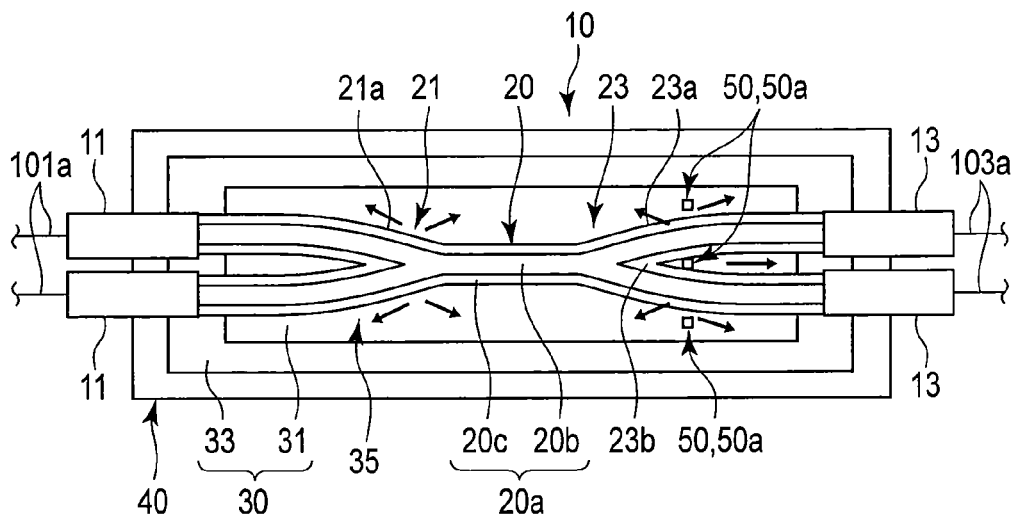
FIG. 2A is a diagram of the optical unit viewed from above in a state where two incident entrances and two emitters are arranged.

Each embodiment of the present invention will now be described in detail with reference to the drawings. For example, some of the drawings omit illustrations of a part of a member for clarification, such as omitting a cover member of an optical fiber 20a in FIG. 2A and the optical fiber 20a in FIG. 2B.

First Embodiment (Configuration)

The first embodiment will be explained with reference to FIG. 1A, FIG. 1B, FIG. 2A, FIG. 2B, FIG. 2C, FIG. 3A, FIG. 3B, FIG. 4A, and FIG. 4B.

(Main Configuration of Optical Unit 10)

As shown in FIG. 1A, the optical unit 10 functions as a light guide member which guides a primary light emitted from alight source 101 to alight converter (light conversion unit) 103. Therefore, the optical unit 10 comprises one or more incident entrances (incident end portions) 11 into which the primary light emitted from the light source 101 enters, and one or more emitters (emission end portions) 13 from which the primary light entered from the incident entrance 11 and guided by the optical unit 10 is emitted. In the present embodiment, at least one of the incident entrance 11 and the emitter 13 is arranged in a plurality of numbers. Therefore, the optical unit 10 also functions as a coupler.

The number of incident entrances 11 and emitters 13 is not limited in particular. In the following is explained an example of a first state in which two incident entrances 11 and two emitters 13 are arranged as shown in FIG. 1A, FIG. 2A, FIG. 2B, and FIG. 2C, a second state in which one incident entrance 11 and two emitters 13 are arranged as shown in FIG. 3A and FIG. 3B, and a third state in which two incident entrances 11 and one emitter 13 are arranged as shown in FIG. 4A and FIG. 4B. Although not illustrated, in the case where the incident entrance 11 and the emitter 13 are arranged in a plurality of numbers, the numbers of the incident entrances 11 and the emitters do not have to be the same.

The incident entrance 11 mentioned above is arranged singularly or in a plurality of numbers (here, branched in two). The same applies to the emitter 13. In this state, each light guide path from the incident entrance 11 to the emitter 13, specifically, an optical element 20 of the optical unit 10 explained later on, is bent in a manner that a part of the light guide path curves. Therefore, for example, a path branched in two indicates a state in which a part of one of the branched paths angles against a center axis of the optical element 20, and a part of the other branched path angles against the center axis of the optical element 20. In other words, for example, not all of one of the paths branched in two is arranged on the same axis as the center axis of the optical element 20.

(Configuration 1 of Optical Unit 10/Optical Element 20)

As shown in FIG. 1A, FIG. 2A, FIG. 2B, FIG. 2C, FIG. 3A, FIG. 3B, FIG. 4A, and FIG. 4B, the optical unit 10 further comprises the optical element 20 which comprises the incident entrance 11 and the emitter 13 mentioned above. The incident entrance 11 is arranged at an end portion of the optical element 20, and the emitter 13 is arranged at the other end portion of the optical element 20. The optical element 20 comprises a light coupler (light coupling portion) 21 which is arranged in the case where a plurality of incident entrances 11 are arranged in the manner shown in FIG. 1A, FIG. 2A, FIG. 2B, FIG. 2C, FIG. 4A, and FIG. 4B, and a light separator (light separating portion) 23 which is arranged in the case where a plurality of emitters 13 are arranged in the manner shown in FIG. 1A, FIG. 2A, FIG. 2B, FIG. 2C, FIG. 3A, and FIG. 3B. The light coupler 21 couples each of the primary lights entering from each of the incident entrances 11 in a manner that each of the primary lights entering from each of the incident entrances 11 is guided towards the emitter 13 side. The light separator 23 separates the primary light towards each of the emitters 13 in a manner that the primary light guided from the incident entrance 11 side is further guided to each of the emitters 13. The light coupler 21 is arranged between the incident entrance 11 and the emitter 13, and the light separator 23 is arranged between the light coupler 21 and the emitter 13.

In the optical unit 10, the optical element 20 functions as a light guide path which guides the primary light from the incident entrance 11 to the emitter 13 via the light coupler 21 and the light separator 23. As shown in FIG. 2A, FIG. 3A, and FIG. 4A, such optical element 20 comprises an optical fiber 20a. The optical element 20 functions as an optical fiber coupler formed by the light coupler 21 and the light separator 23. The optical fiber 20a of the optical element 20 comprises, for example, a core 20b, a cladding 20c which has a refractive index lower than that of the core 20b and covers an outer periphery of the core 20b, and an unillustrated cover member which covers an outer periphery of the cladding 20c. Since the incident entrance 11 and the emitter 13 are arranged, both ends of the optical fiber 20a are made singly or are divided into a plurality of branches (here, into two branches) in accordance with the number of incident entrances 11 and the number of emitters 13.

As mentioned above, the optical element 20 comprising the incident entrance 11, the emitter 13, and the optical fiber 20a functions as a light guide member which is arranged between the light source 101 and the light converter 103, and guides light from the light source 101 to the light converter 103. In other words, the optical element 20 is arranged also for guiding light, but is not arranged only for the purpose of other than guiding light, for example, as a configuration dedicated for detection.

Generally, in the optical element 20 functioning as the optical fiber coupler, there is a centralized coupling type which couples the optical fiber cores directly, and a distributed coupling type which has the optical fiber cores mode-coupled by making them adjacent at a wavelength level. The optical element 20 of the present embodiment is applicable to both the centralized coupling type and the distributed coupling type. Here, the cores, for example, indicate the core 20b of the optical element 20 and a core of a first light guide member (first light guide) 101a mentioned later on, and the core 20b of the optical element 20 and a core of a second light guide member (second light guide) 103a mentioned later on.

(Configuration 2 of Optical Unit 10/Fixed Substrate Portion 30/First Exterior Member 40)

As shown in FIG. 2A, FIG. 2B, FIG. 2C, FIG. 3A, FIG. 3B, FIG. 4A, and FIG. 4B, the optical unit 10 further comprises a fixed substrate portion 30 on which the optical element 20 is arranged in a manner that the optical element 20 comprising the light coupler 21 and the light separator 23 is arranged to be positioned on a hollow portion 35 of the fixed substrate portion 30, and a first exterior member 40 installed exterior to the incident entrance 11, the emitter 13, the optical element 20, and the fixed substrate portion 30 in a manner that the incident entrance 11 and the emitter 13 penetrate the first exterior member 40.

As shown in FIG. 2A, FIG. 2B, FIG. 2C, FIG. 3A, FIG. 3B, FIG. 4A, and FIG. 4B, for example, the fixed substrate portion 30 comprises a rectangular flat plate portion 31, and a rectangular frame portion 33 which stands upright with respect to the flat plate portion 31 and is arranged integrally with the flat plate portion 31. Therefore, in the fixed substrate portion 30, the flat plate portion 31 serves as a bottom portion, and the hollow portion 35 is arranged surrounded by the flat plate portion 31 and the frame portion 33.

As shown in FIG. 2A, FIG. 2B, FIG. 2C, FIG. 3A, FIG. 3B, FIG. 4A, and FIG. 4B, the incident entrance 11 is mounted on the frame portion 33, and is fixed on the frame portion 33 by an unillustrated adhesive member.

As shown in FIG. 2A, FIG. 2B, FIG. 2C, FIG. 3A, FIG. 3B, FIG. 4A, and FIG. 4B, the emitter 13 is mounted on the frame portion 33, and is fixed on the frame portion 33 by an unillustrated adhesive member.

Therefore, a part of the optical element 20 including the light coupler 21 and the light separator 23, and positioned between the incident entrance 11 and the emitter 13 in the axial direction of the optical element 20, is arranged at the hollow portion 35 positioned inside the frame portion 33, and serves as a portion floating in the hollow portion 35. This portion does not come in contact with the fixed substrate portion 30 and the first exterior member 40.

The incident entrance 11 and the emitter 13 serve as fixed end portions. The fixed end portions immovably fix the optical element 20 which serves as a light guide path. The fixed substrate portion 30 secures mechanical intensity of the optical element 20.

As shown in FIG. 2A, FIG. 2B, FIG. 2C, FIG. 3A, FIG. 3B, FIG. 4A, and FIG. 4B, the first exterior member 40 would be installed exterior to each constituent member of the optical unit 10, including the hollow portion 35. For example, the first exterior member 40 has thermal tolerance, and is formed by a member which is less affected by thermal expansion.

(Configuration 3 of Optical Unit 10/Detector 50)

As shown in FIG. 1A, FIG. 2A, FIG. 2B, FIG. 2C, FIG. 3A, FIG. 3B, FIG. 4A, and FIG. 4B, the optical unit 10 further comprises a detector (detection portion) 50 which, in the present embodiment, directly detects the primary light (hereinafter, referred to as leakage light) leaking outside of the light guide path from the light guide path, including the light coupler 21 and the light separator 23 between the incident entrance 11 and the emitter 13. In this case, the leakage light is, for example, the primary light leaking outside of the cladding 20c of the optical element 20 from the cladding 20c of the optical element 20. The outside indicates an outside on the outer peripheral surface side of the cladding 20c, and not the core 20b side on an inner peripheral surface side of the cladding 20c. In the present embodiment, as shown in FIG. 2A, FIG. 2B, FIG. 2C, FIG. 3A, FIG. 3B, FIG. 4A, and FIG. 4B, the detector 50 comprises a detection member 50a which detects a light intensity of the leakage light directly. The detection member 50a comprises, for example, at least one of a photodiode and an imaging element (for example, CCD). The detector 50 detects the primary light by the photodiode receiving the primary light. The detector 50 detects the primary light by the imaging element imaging the primary light as an image.

As shown in FIG. 2B, FIG. 2C, FIG. 3B, and FIG. 4B, the detector 50 is arranged at a position away from the optical element 20 in a manner facing the optical element 20 in a height direction of the optical unit 10. In this case, the detector 50 is arranged in a range where the leakage light leaking out from at least a part of the light coupler 21 and the light separator 23 can be reached. At least one detector 50 is arranged at least one of near the light coupler 21 in a manner facing the light coupler 21 in the height direction of the optical unit 10, and near the light separator 23 in a manner facing the light separator 23 in the height direction of the optical unit 10.

As shown in FIG. 4B, for example, the detector 50 is arranged near the light coupler 21 so as to be able to detect the leakage light leaking out from the light coupler 21. In this case, for example, the detector 50 is arranged on both the surface of the flat plate portion 31 of the fixed substrate portion 30 and the inner periphery of the first exterior member 40 so as to face the light coupler 21 in the height direction of the optical unit 10. The detector 50 may be arranged on at least one of the surface and the inner periphery. In this manner, the detector 50 is not arranged directly on the optical element 20, the detector 50 is arranged in a range where the leakage light leaking out from the light coupler 21 may be reached.

Figure 2B:
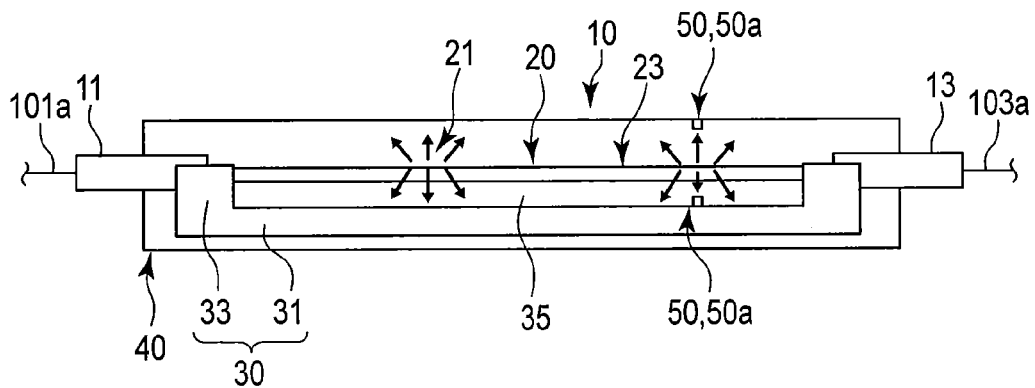
FIG. 2B is a diagram of the optical unit shown in FIG. 2A viewed from the side.
Figure 3A:
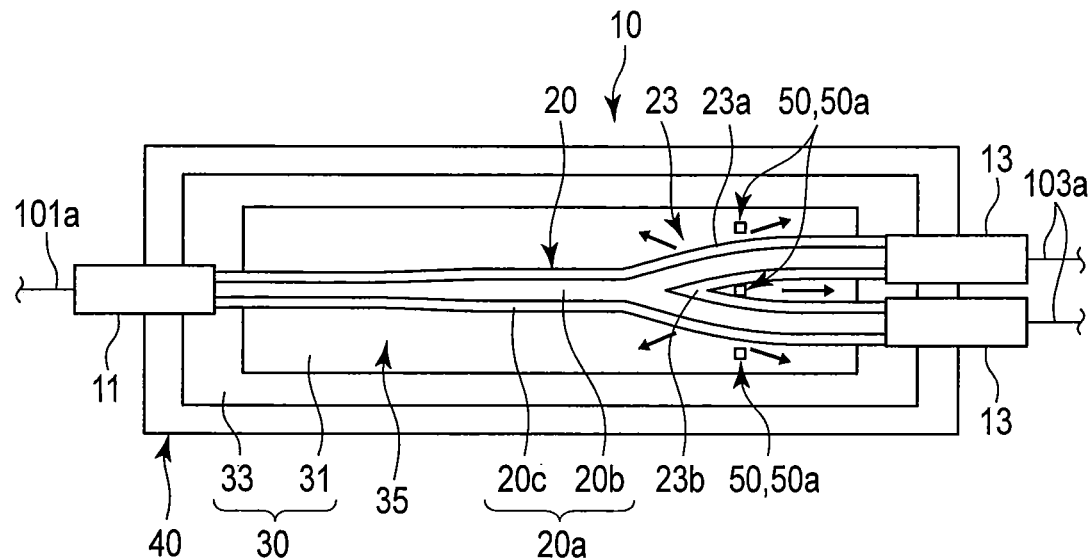
FIG. 3A is a diagram of the optical unit viewed from above in a state where one incident entrance and two emitters are arranged.
Figure 3B:
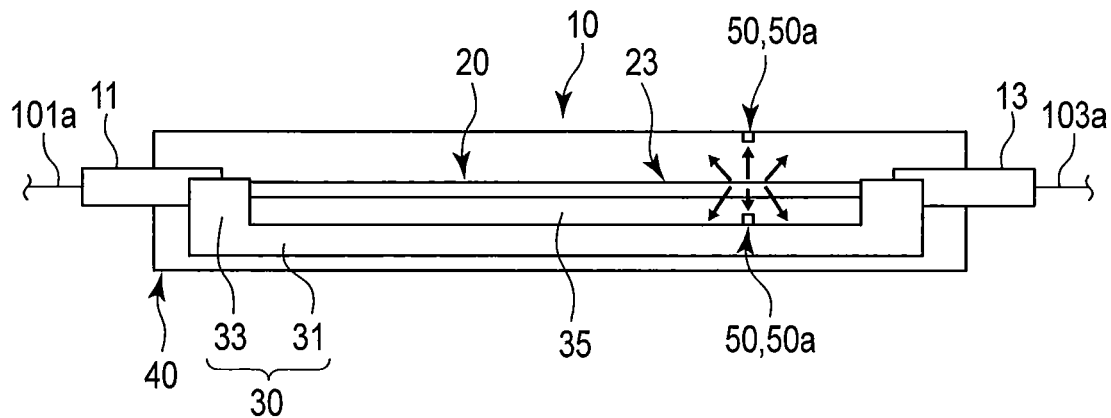
FIG. 3B is a diagram of the optical unit shown in FIG. 3A viewed from the side.
Figure 4A:
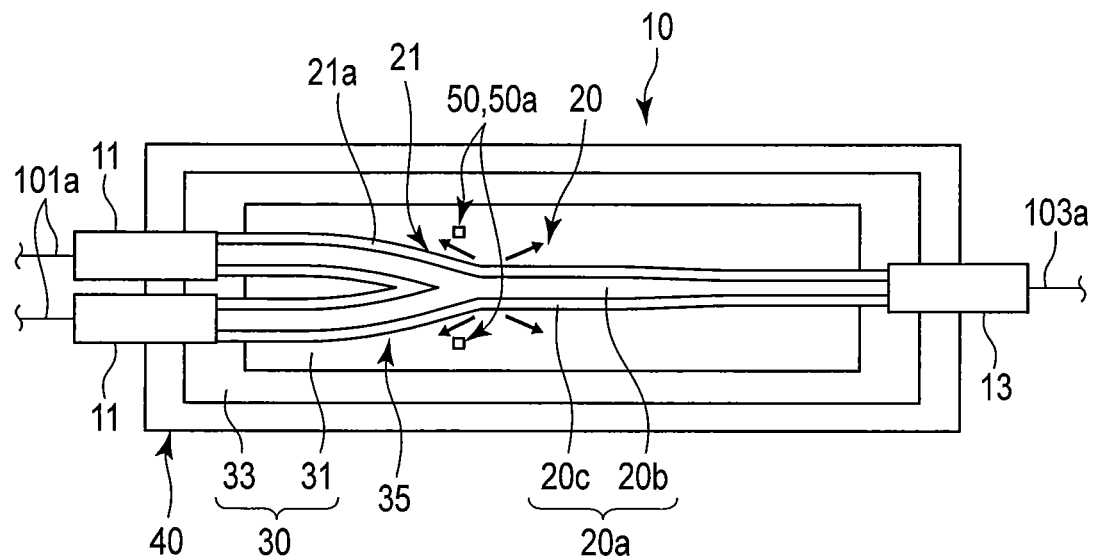
FIG. 4A is a diagram of the optical unit viewed from above in a state where two incident entrances and one emitter are arranged.
Figure 4B:
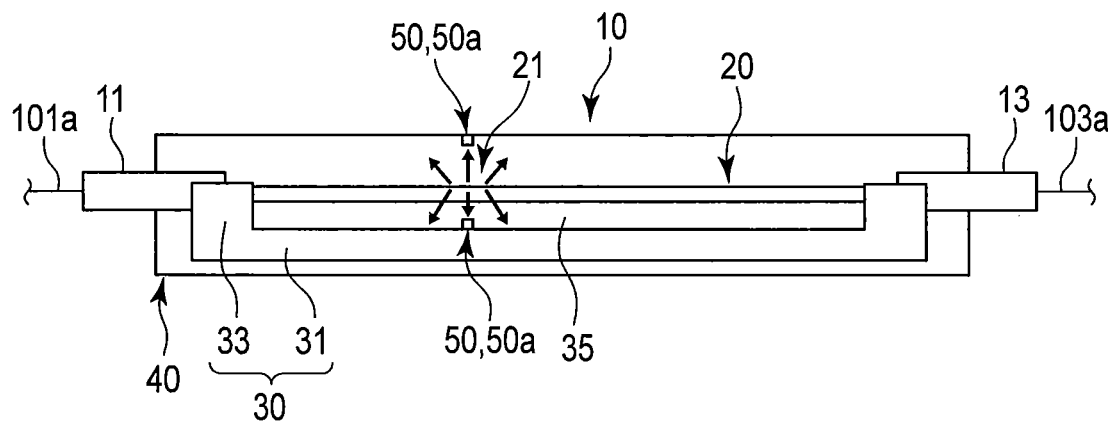
FIG. 4B is a diagram of the optical unit shown in FIG. 4A viewed from the side.

As shown in FIG. 2B and FIG. 3B, for example, the detector 50 may be arranged near the light separator 23 in a manner so that the detector 50 can detects the leakage light leaking out from the light separator 23. In this case, for example, the detector 50 is arranged on both the surface of the flat plate portion 31 of the fixed substrate portion 30 and the inner periphery of the first exterior member 40 in a manner facing the light separator 23 in the height direction of the optical unit 10. The detector 50 may be arranged on at least one of the surface and the inner periphery. In this manner, the detector 50 is not directly arranged on the optical element 20, the detector 50 is in a range where the leakage light leaking out from the light separator 23 may be reached.

Figure 2C:
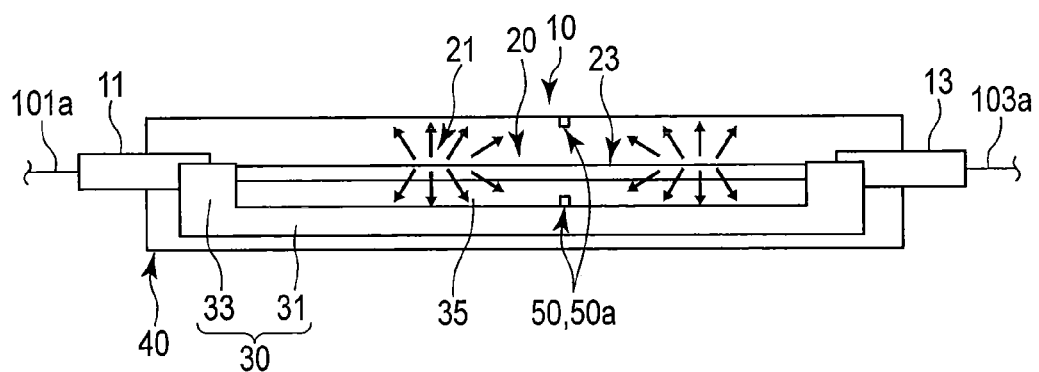
FIG. 2C is a diagram of the optical unit shown in FIG. 2A viewed from the side in a state where a detector is arranged between a light coupler and a light separator.

As shown in FIG. 2C, for example, the detector 50 may be arranged between the light separator 23 and the light coupler 21 in the axial direction of the optical element 20 so that the detector 50 can detect at least one of the leakage light leaking out from the light coupler 21 and the leakage light leaking from the light separator 23. In this case, for example, the detector 50 is arranged on both the surface of the flat plate portion 31 of the fixed substrate portion 30, and the inner periphery of the first exterior member 40 in a manner facing the optical element 20 in the height direction of the first exterior member 40. The detector 50 may be arranged on at least one of the surface and the inner periphery. In this manner, the detector 50 is arranged in a range where the leakage light leaking out from the light coupler 21 and the leakage light leaking out from the light separator 23 may be reached.

In the above, as shown in FIG. 2A, FIG. 3A, and FIG. 4A, a plurality of detectors 50 are arranged on the flat plate portion 31 of the fixed substrate portion 30; however, at least one detector 50 needs to be arranged. Although not illustrated, in the same manner as the above, at least one detector 50 should be arranged on the inner periphery of the first exterior member 40.

(Mechanism of Primary Light Leaking Out from Light Coupler 21 and Light Separator 23)

As shown in FIG. 2A, FIG. 3A, and FIG. 4A, in the optical element 20 of the present embodiment, the end portion of the optical element 20 is divided into a plurality of branches in accordance with the number of incident entrances 11 and emitters 13. In this manner, the light coupler 21 and the light separator 23 are created.

As shown in FIG. 2A and FIG. 4A, at the light coupler 21, the optical element 20 has a coupling side curve-shaped portion 21a which is formed by the bent light coupler 21, and is a part of the light coupler 21. As shown in FIG. 2A and FIG. 3A, at the light separator 23, the optical element 20 has a separating side curve-shaped portion 23a which is formed by the bent light separator 23, and is a part of the light separator 23.

As shown in FIG. 2A and FIG. 4A, the primary light refracts at the cladding 20c of the coupling side curve-shaped portion 21a, which causes a part of the primary light to leak outside of the optical element 20 from the light coupler 21. At this time, as shown in FIG. 2A, FIG. 2B, FIG. 2C, FIG. 4A, and FIG. 4B, the leakage light travels in all directions such as in the forward/backward, left/right and up/down directions. The forward/backward direction indicates the axial direction of the optical element 20, which is, for example, the left/right direction in the illustrations of FIG. 2A and FIG. 2B. The left/right direction indicates a width direction of the optical element 20, which is, for example, the up/down direction in the illustration of FIG. 2A, and is a direction perpendicular to the axial direction of the optical element 20. The up/down direction indicates a height direction of the optical element 20, which is, for example, the up/down direction in the illustration of FIG. 2B, and indicates a direction perpendicular to the axial direction and the width direction of the optical element 20.

When the primary light travels to the light separator 23, as shown in FIG. 2A and FIG. 3A, a part of the primary light leaks outside of the optical element 20 from the light separator 23 by a stem portion 23b at which the light separator 23 is divided into two branches. Another part of the primary light refracts at the cladding 20c of the separating side curved-shaped portion 23a of the light separator 23, which causes the part of the primary light to leak outside of the optical element 20 from the light separator 23. At this time, as shown in FIG. 2A, FIG. 2B, FIG. 2C, FIG. 3A, and FIG. 3B, and in a likewise manner mentioned above, the leakage light travels in all directions such as in the forward/backward, left/right and up/down directions.

The mechanism mentioned above is confirmed by a simulation.

In consideration of the matters mentioned above, the detector 50 is arranged near the light coupler 21, specifically, in the periphery of and centering on the light coupler 21 so that the leakage light leaking out from the light coupler 21 may be reached. The leakage light leaks out more on the front (emitter 13) side than on the back (incident entrance 11) side of the light coupler 21 from the light coupler 21. Therefore, it is more preferable for the detector 50 to be arranged in the front than in the back of the light coupler 21. The same applies to the detector 50 in the light separator 23.

(Configuration of Periphery of Optical Unit 10)

As shown in FIG. 1A and FIG. 1B, the optical unit 10 mentioned above is incorporated in the endoscope system 200 which comprises the endoscope 201, and a light source device 203 and a controller (control device) 205 connected to the endoscope 201. The endoscope system 200 further comprises the light source 101, the light converter 103 which performs light conversion on the primary light emitted from the emitter 13 and emits it externally, and a calculator (calculation portion) 105 which calculates the light intensity on the light guide path based on the leakage light detected by the detector 50 of the optical unit 10. The light source 101 is arranged in the light source device 203. The light converter 103 is arranged at a distal end portion of an insertion portion 201a of the endoscope 201. The calculator 105 is arranged in the controller 205. The calculator 105 and the controller 205 have, for example, a hardware circuitry including ASCI.

As shown in FIG. 1A, the incident entrance 11 is optically connected to the light source 101 so that the primary light emitted from the light source 101 enters the incident entrance 11. The relationship between the light source 101 and the incident entrance 11 is that the primary light emitted from one light source 101 enters one incident entrance 11. The primary light emitted from one light source 101 may also be separated and enter each incident entrance 11. In this manner, the relationship between the number of light sources 101 and the number of incident entrances 11 is not particularly limited. The light source 101 comprises, for example, a laser diode which emits the primary light.

As shown in FIG. 1A, the incident entrance 11 is connected indirectly with the light source 101 via a first light guide member 101a which guides the primary light emitted from the light source 101. The first light guide member 101a comprises, for example, an optical fiber. For example, except for the end portion of the first light guide member 101a connected to the incident entrance 11, most of the first light guide member 101a is covered by an unillustrated cover member. Although unillustrated, the first light guide member 101a comprises, for example, a core, and a cladding which has a lower refractive index than that of the core and covers an outer periphery surface of the core. For example, the incident entrance 11 may be connected directly to the light source 101.

As shown in FIG. 1A, the emitter 13 is optically connected to the light converter 103 so that the primary light guided by the optical unit 10 enters the light converter 103. The relationship between the emitter 13 and the light converter 103 is such that the primary light emitted from one emitter 13 enters one light converter 103. It may also be that the primary light emitted from each emitter 13 enters one light converter 103. In this manner, the relationship between the number of emitters 13 and the number of light converters 103 is not particularly limited.

As shown in FIG. 1A, the emitter 13 is connected indirectly with the light converter 103 via a second light guide member 103a which guides the primary light emitted from the emitter 13. The second light guide member 103a comprises, for example, an optical fiber. For example, except for the end portion of the second light guide member 103a connected to the emitter 13, most of the second light guide member 103a is covered by an unillustrated cover member. The second light guide member 103a comprises, for example, a core, and a cladding which has a lower refractive index than that of the core and covers an outer periphery surface of the core. For example, the emitter 13 may be connected directly to the light converter 103.

The light converter 103 converts the optical characteristics of the primary light to generate a secondary light, and emits the secondary light as an illumination light. The conversion of the optical characteristics includes, for example, a first function which converts a light spectrum, a second function which converts light distribution, and a third function which converts polarized light. The first function refers to, for example, a fluorescent body including wavelength conversion, electroluminescence, light emission by a semiconductor, a light filter, and a secondary harmonic generation. The second function refers to light diffusion and lens effect, etc.

As shown in FIG. 1B, such optical unit 10 is, for example, built into the endoscope 201. Specifically, the optical unit 10 is arranged in one of the distal end portion of an insertion portion 201a, an operation portion 201b, a connector (connection portion) 201d of a universal cord 201c, and the light source device 203 to which the connector 201d is connected.

For example, the first light guide member 101a is arranged between the light source 101 and the optical unit 10, the second light guide member 103a is arranged between the optical unit 10 and the distal end portion of the insertion portion 201a, and the light converter 103 is arranged at the distal end portion of the insertion portion 201a.

In the case where the optical unit 10 is arranged, for example, in the operation portion 201b, the first light guide member 101a is arranged in the connector 201d, the universal cord 201c, and the operation portion 201b, and the second light guide member 103a is arranged in the operation portion 201b and the insertion portion 201a. The primary light is emitted from the light source 101 which the light source device 203 comprises, enters the light converter 103 via the first light guide member 101a, the optical unit 10, and the second light guide member 103a, is light converted by the light converter 103, and emitted externally from the distal end portion of the insertion portion 201a as the secondary light.

Prior to actually using the optical unit 10 in a state where, for example, it is mounted on the endoscope 201 or the light source device 203, the calculator 105 calculates in advance the light intensity of the primary light emitted from the light source 101. The calculator 105 may acquire information regarding the light intensity of the primary light emitted from the light source 101 from a light source controller (light source control portion) 209. Simultaneously, the calculator 105 calculates in advance the light intensity of the leakage light at the light coupler 21, and the light intensity of the leakage light at the light separator 23, based on the leakage light detected by the detector 50 as a detection result. The degree of light intensity of the leakage light varies depending on, for example, how much the optical element 20 is bent, and the light intensity of the primary light entering the incident entrance 11. The calculator 105 calculates in advance the correlation between the light intensity of the primary light emitted from the light source 101 and the light intensity of the leakage light at the light coupler 21, and the correlation between the light intensity of the primary light emitted from the light source 101 and the light intensity of the leakage light at the light separator 23.

As shown in FIG. 1A and FIG. 1B, the controller 205 comprises a recording unit 205a which records the detection result detected by the detector 50 and the correlation above which is a calculation result calculated in advance by the calculator 105. The recording unit 205a has a recorder. The controller 205 further comprises a light source controller 209 which controls the light source 101 based on, for example, the detection result detected by the detector 50 and the correlation recorded in the recording unit 205a, so that the light intensity of the leakage light becomes a desired value, and the light intensity of the primary light guided to the light converter 103 becomes desirable. For example, the light source controller 209 controls a drive current amount, etc. of the light source 101, so that the primary light emitted from the light source 101 has an increased or decreased output amount based on the detection result and the correlation. The endoscope system 200 further comprises a display unit 207 which displays the detection result and the correlation, etc. The display unit 207 has a monitor.

(Operation)

The light emitted from the light source 101 is guided up to the incident entrance 11. The light enters the optical element 20 from the incident entrance 11.

As shown in FIG. 3A and FIG. 3B, in the case where one incident entrance 11 is arranged, and the light coupler 21 is not arranged, the primary light is guided toward the emitter 13 by the optical element 20.

As shown in FIG. 2A, FIG. 2B, FIG. 2C, FIG. 4A, and FIG. 4B, in the case where a plurality of incident entrances 11 and the light coupler 21 are arranged, each of the primary lights refracts at the coupling side curve-shaped portion 21a at the light coupler 21. In this manner, a part of each of the primary lights leaks outside of the optical element 20 from the light coupler 21. The other parts of each of the primary lights are coupled at the light coupler 21, and are guided toward the emitter 13 by the optical element 20 in a coupled state.

As shown in FIG. 4A and FIG. 4B, the detector 50 arranged near the light coupler 21 detects the leakage light leaking out from the light coupler 21. Specifically, the detector 50 receives the primary light, or images the primary light as an image.

The detection result of the detector 50 is displayed, for example, on the display unit 207. The calculator 105 calculates the light intensity of the primary light emitted from the light source 101 with respect to the light intensity of the detected leakage light based on this detection result and the calculation result calculated in advance. The calculation result indicates the correlation between the light intensity emitted from the light source 101 and the light intensity of the leakage light at the light coupler 21 recorded in the recording unit 205a. The calculation result calculated by the calculator 105 is displayed on the display unit 207.

As shown in FIG. 4A and FIG. 4B, in the case where one emitter 13 is arranged, and the light separator 23 is not arranged, the primary light is emitted from the emitter 13 and guided to the light converter 103. The primary light is light converted by the light converter 103 and emitted toward the outside.

As shown in FIG. 2A, FIG. 2B, FIG. 2C, FIG. 3A, and FIG. 3B, in the case where a plurality of emitters 13 and the light separator 23 are arranged, a part of the primary light leaks outside of the optical element 20 from the light separator 23 by the stem portion 23b at which the light separator 23 is divided into two branches. Another part of the primary light refracts at the separating side curve-shaped portion 23a at the light separator 23. This causes a part of the primary light to leak outside of the optical element 20 from the light separator 23. The other parts of the primary light are separated by the light separator 23, and travels to each emitter 13. The primary light is emitted from the emitter 13 and guided to the light converter 103. The primary light is light converted into a secondary light by the light converter 103 and is emitted toward the outside.

As shown in FIG. 2A, FIG. 2B, FIG. 2C, FIG. 3A, and FIG. 3B, the detector 50 arranged near the light separator 23 detects the leakage light leaking out from the light separator 23. Specifically, the detector 50 receives the primary light, or images the primary light as an image.

The detection result of the detector 50 is displayed, for example, on the display unit 207. The calculator 105 calculates the light intensity of the primary light emitted from the light source 101 with respect to the light intensity of the detected leakage light, based on this detection result and the calculation result calculated in advance. The calculation result indicates the correlation between the light intensity of the primary light emitted from the light source 101 and the light intensity of the leakage light at the light separator 23 recorded in the recording unit 205a. The calculation result calculated by the calculator 105 is displayed on the display unit 207.

(Advantages)

In the present embodiment, the optical element 20 is arranged also for guiding light, but is not arranged only for purposes other than guiding light; for example, as a configuration dedicated for detection. Accordingly, the present embodiment is capable of detecting light intensity by using leakage light without having a configuration dedicated for detection arranged, and preventing light loss for detection from occurring.

The present embodiment is capable of reliably detecting the light intensity of the leakage light at the light coupler 21 by the detector 50 arranged near the light coupler 21. The present embodiment is capable of detecting the light intensity of the primary light guided inside the optical element 20 based on this detection result and the correlation between the light intensity of the primary light emitted from the light source 101 and the light intensity of the leakage light at the light coupler 21 recorded in the recording unit 205a. The present embodiment is capable of measuring the light intensity of the primary light emitted from the light source 101 with respect to the light intensity of the detected leakage light based on this detection result and the correlation between the light intensity of the primary light emitted from the light source 101 and the light intensity of the leakage light at the light coupler 21 recorded in the recording unit 205a.

The present embodiment is capable of reliably detecting the light intensity of the leakage light at the light separator 23 by the detector 50 arranged near the light separator 23. The present embodiment is capable of detecting the light intensity of the primary light guided inside the light converter 103 based on this detection result and the correlation between the light intensity of an emission light emitted from the light source 101 and the light intensity of the leakage light at the light separator 23 recorded in the recording unit 205a. The present embodiment is capable of measuring the light intensity of the primary light emitted from the emitter 13 with respect to the light intensity of the detected leakage light based on this detection result and the correlation between the light intensity of the emission light emitted from the light source 101 and the light intensity of the leakage light at the light separator 23 recorded in the recording unit 205a.

For example, suppose the detector 50 detects the leakage light in a state where the optical unit 10 is arranged at the distal end portion of the insertion portion 201a. In this case, it can be determined whether an abnormality has occurred at the distal end portion. In this manner, the present embodiment is capable of determining the abnormality in accordance with the arrangement position of the optical unit 10.

In the present embodiment, as the optical unit 10 is arranged closer to the distal end portion side of the insertion portion 201a than to the connector 201d, the light intensity at the distal end portion side can be reliably detected. In the present embodiment, as the optical unit 10 is arranged closer to the connector 201d side than to the distal end side of the insertion portion 201a, an arrangement space for the optical unit 10 can be easily ensured.

The present embodiment is capable of controlling the light intensity of the primary light emitted from the optical unit 10 by controlling an output amount of the light source 101 by the light source controller 209 based on the detection result and the correlation.

For the detector 50 to detect the leakage light easily the leakage amount of primary light should preferably be large. Therefore, at the light coupler 21 and the light separator 23, an unillustrated cover member of the optical element 20 may be removed, or the cladding 20c of the optical element 20 may be thinly formed.

The detector 50 should be arranged away from the optical element 20 in a manner that the leakage light reaches the detector 50. Therefore, the detector 50 may be arranged, for example, on an inner periphery surface of a frame portion 33, at the sides of the light coupler 21 and the light separator 23. The detector 50 may also be arranged to be in close contact with the light coupler 21 and the light separator 23.

FIRST MODIFIED EXAMPLE OF FIRST EMBODIMENT

In the present modified example, a fixed substrate portion 30 may be formed by a member capable of transmitting the primary light. This member comprises, for example, a transparent quartz glass.

Figure 5A:
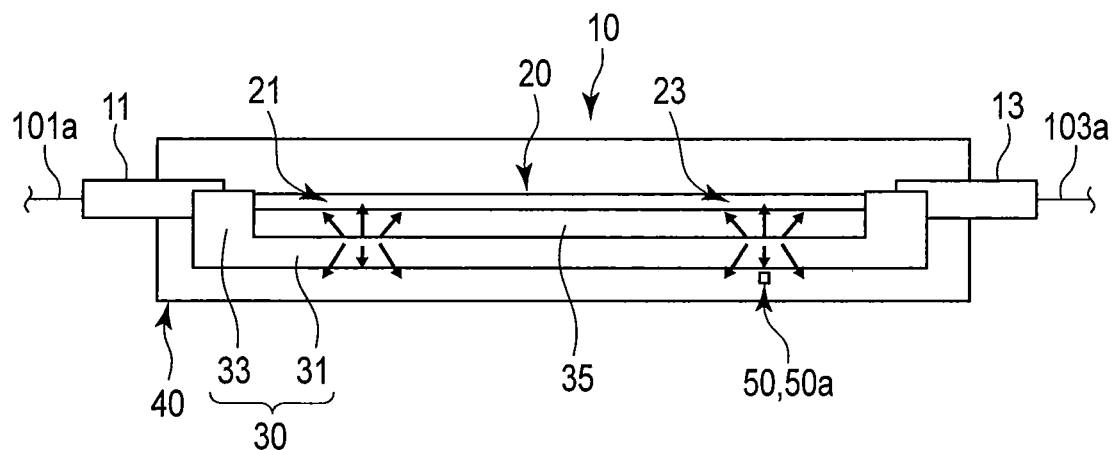
FIG. 5A is a diagram of an optical unit in a first modified example of the first embodiment viewed from the side.

In this case, as shown in FIG. 5A, since the leakage light leaking out from the light coupler 21 and the light separator 23 is transmittable through the fixed substrate portion 30, the detector 50 can be arranged on the back surface of the flat plate portion 31 of the fixed substrate portion 30.

In this manner, the present modified example can enhance the degree of freedom in arranging the detector 50.

SECOND MODIFIED EXAMPLE OF FIRST EMBODIMENT

In the present modified example, the first exterior member 40 may be formed by a member capable of transmitting the primary light. This member comprises, for example, a transparent quartz glass.

Figure 5B:
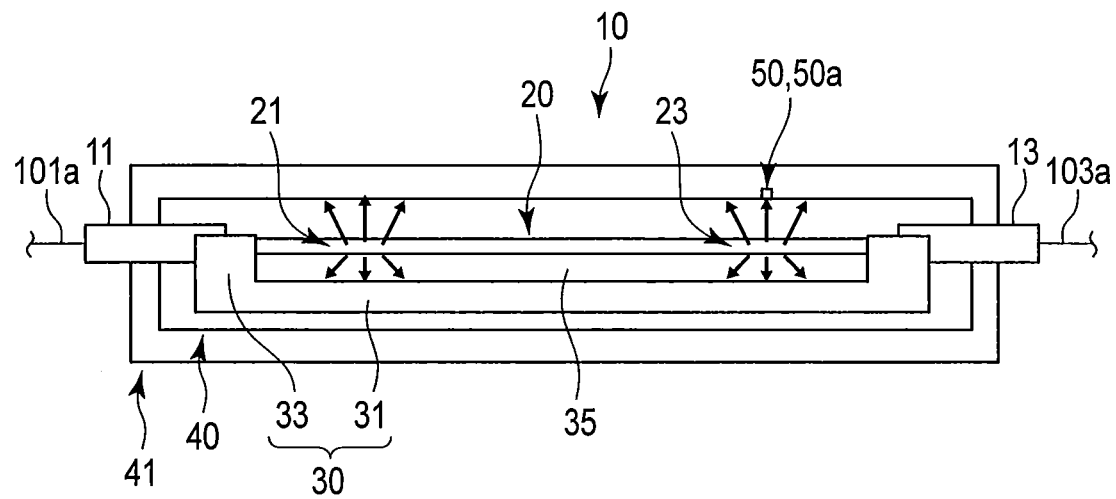
FIG. 5B is a diagram of an optical unit in a second modified example of the first embodiment viewed from the side.

In this case, as shown in FIG. 5B, since the leakage light leaking out from the light coupler 21 and the light separator 23 is transmittable through the first exterior member 40, the detector 50 can be arranged on the outer periphery surface of the first exterior member 40.

In this case, as shown in FIG. 5B, the optical unit 10 further comprises a second exterior member 41 which is externally installed to an incident entrance 11, an emitter 13, an optical element 20, a fixed substrate portion 30, and the first exterior member 40. The second exterior member 41 shields the primary light so that the primary light transmitted through the first exterior member 40 is not transmitted through the second exterior member 41 and emitted outside of the second exterior member 41.

In this manner, the present modified example can enhance the degree of freedom in arranging the detector 50.

Second Embodiment (Configuration)

Mainly with reference to FIG. 6, only configurations different from the configurations of the first embodiment will be explained below. Configurations similar to those described in the first embodiment will be denoted by the same reference symbols as used above, and a detailed description of such structures will be omitted.

Figure 6:
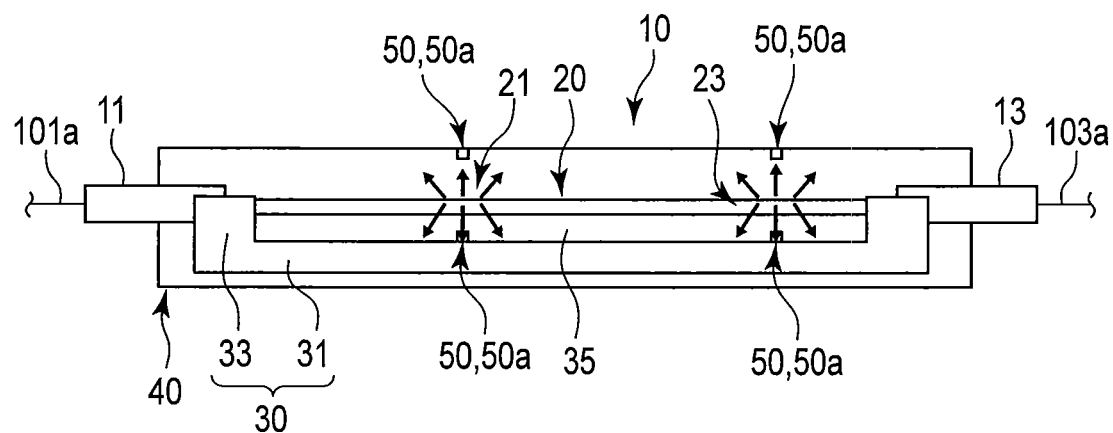
FIG. 6 is a diagram of an optical unit in a second embodiment viewed from the side.

As shown in FIG. 6, for example, the detector 50 is arranged near the light coupler 21 so that can detect the leakage light leaking out from the light coupler 21, and near the light separator 23 so that it can detect the leakage light leaking out from the light separator 23.

In this case, as show in FIG. 6, for example, the detector 50 is arranged on both the surface of the flat plate portion 31 of the fixed substrate portion 30 and the inner periphery surface of the first exterior member 40 in a manner facing the light coupler 21 in the height direction of the optical unit 10. The detector 50 may be arranged on at least one of the surface and the inner periphery surface.

In this case, as shown in FIG. 6, for example, the detector 50 is arranged on both the surface of the flat plate portion 31 of the fixed substrate portion 30 and the inner periphery surface of the first exterior member 40 in a manner facing the light separator 23 in the height direction of the optical unit 10. The detector 50 may be arranged on at least one of the surface and the inner periphery surface.

In the above, as shown in FIG. 2A, FIG. 3A, and FIG. 4A, at least one detector 50 should be arranged on the flat plate portion 31 of the fixed substrate portion 30. Although not illustrated, in the same manner as the above, at least one detector 50 should be arranged on the inner periphery surface of the first exterior member 40.

The calculator 105 calculates a difference between the detection result of the detector 50 at the light coupler 21 and the detection result of the detector 50 at the light separator 23.

(Advantage)

In the present embodiment, by arranging the detector 50 at two places, near the light coupler 21 and near the light separator 23, the calculator 105 is capable of detecting the difference. Accordingly, in the present embodiment, this difference allows at least one of the malfunction and the degradation of the optical element 20 itself positioned between the light coupler 21 and the light separator 23 in the axial direction of the optical element 20 to be detected.

FIRST MODIFIED EXAMPLE OF SECOND EMBODIMENT (Configuration)

Figure 7:
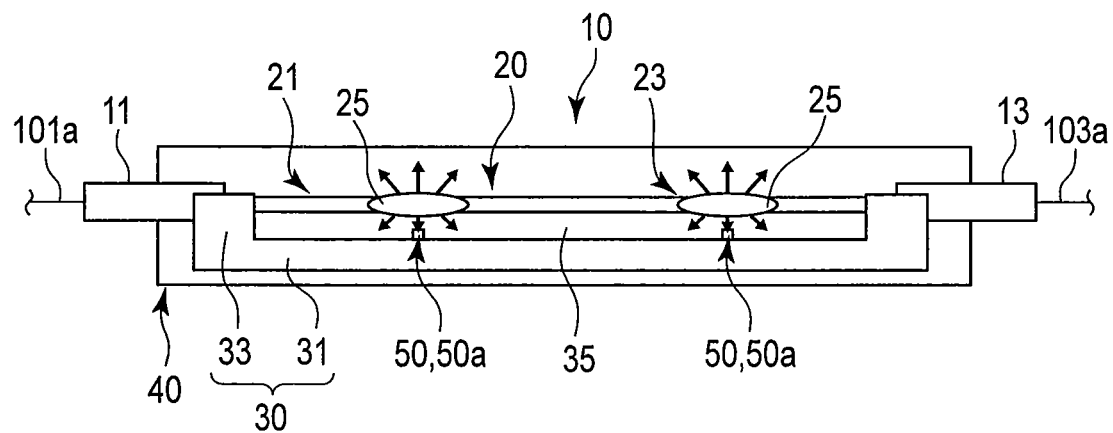
FIG. 7 is a diagram of an optical unit in a first modified example of the second embodiment viewed from the side.

As shown in FIG. 7, for example, the optical element 20 further comprises a refractive index member 25 which is arranged at a portion where the leakage light leaks out, such as at the light coupler 21 and the light separator 23, and has a refractive index equal to or larger than a refractive index of a cladding 20c which serves as an outermost layer of the optical element 20. For example, the refractive index member 25 comprises an adhesive resin.

Since the refractive index of the refractive index member 25 is at least the same as the refractive index of the cladding 20c, the refractive index member 25 generates a large light intensity of leakage light.

By arranging the refractive index member 25 at the light coupler 21, the refractive index member 25 reinforces the strength of the light coupler 21 which has a low strength in the optical element 20. The refractive index member 25 protects the light coupler 21 when stress is applied to the optical element 20. The refractive index member 25 fixes the light coupler 21 to the fixed substrate portion 30.

The same also applies to the light separator 23.

(Advantages)

In the present modified example, the refractive index member 25 is capable of generating a large amount of leakage light. Accordingly, in the present modified example, the detector 50 is capable of more reliably detecting the primary light.

In the modified example, the refractive index member 25 is capable of reinforcing the strength of the light coupler 21 which has low strength in the optical element 20. In the present modified example, the refractive index member 25 is capable of protecting the light coupler 21 when stress is applied on the optical element 20. In the present modified example, the refractive index member 25 is capable of fixing the light coupler 21 to the fixed substrate portion 30. The same also applies to the light separator 23.

SECOND MODIFIED EXAMPLE OF SECOND EMBODIMENT (Configuration)

As shown in FIG. 8A, in the case where the detector 50 is arranged near the light guide path (the optical element 20a) positioned between each of the incident entrances 11 and the light coupler 21, the detector 50 is arranged near the light guide path positioned between one of the incident entrances 11 and the light coupler 21, and near the light guide path positioned between the other incident entrances 11 and the light coupler 21. In this manner, for example, the detector 50 is arranged between the incident entrance 11 and the light coupler 21 in the axial direction of the optical element 20.

In this case, for example, the detector 50 is arranged near the light guide path (the optical element 20a) so as to be able to detect the leakage light. As shown in FIG. 8B, for example, the detector 50 is arranged on both the surface of the flat plate portion 31 of the fixed substrate portion 30 and the inner periphery surface of the first exterior member 40 in a manner facing near the light guide path in the height direction of the optical unit 10. The detector 50 may be arranged on at least one of the surface and the inner periphery surface. In this manner, the detector 50 is arranged in a range where the leakage light leaking out from near the light guide path can be reached, and not directly on the optical element 20.

As shown in FIG. 8A, in the case where the detector 50 is arranged near the light guide path (optical element 20a) positioned between the light separator 23 and each of the emitters 13, the detector 50 is arranged near the light guide path positioned between the light separator 23 and one of the emitters 13, and near the light guide path positioned between the light separator 23 and the other emitters 13. In this manner, for example, the detector 50 is arranged between the light separator 23 and the emitter 13 in the axial direction of the optical element 20.

In this case, for example, the detector 50 is arranged near the light guide path (the optical element 20a) so as to be able to detect the leakage light. As shown in FIG. 8B, for example, the detector 50 is arranged on both the surface of the flat plate portion 31 of the fixed substrate portion 30 and the inner periphery surface of the first exterior member 40 in a manner facing near the light guide path in the height direction of the optical unit 10. The detector 50 may be arranged on at least one of the surface and the inner periphery surface. In this manner, the detector 50 is arranged in a range where the leakage light leaking out from near the light guide path can be reached, and not directly on the optical element 20.

In the above, as shown in FIG. 8A, at least one detector 50 should be arranged on the flat plate portion 31 of the fixed substrate portion 30. Although not illustrated, in the same manner as the above, at least one detector 50 should be arranged on the inner periphery surface of the first exterior member 40.

For the detector 50 to detect the leakage light easily the leakage amount of primary light should preferably be large. Therefore, an unillustrated cover member of the optical element 20 may be removed or the cladding 20c of the optical element 20 may be thinly formed at a part of the optical element 20 positioned between the incident entrance 11 and the light coupler 21, and a part of the optical element 20 positioned between the emitter 13 and the light separator 23, which serves as the light guide path mentioned above.

(Advantages)

In the present modified example, the detector 50 is capable of detecting the light intensity of the leakage light at each of the incident entrances 11 sides. In the present modified example, the detector 50 is capable of detecting the ratio between the light intensity of the leakage light at one of the incident entrance 11 sides and the light intensity of the leakage light at the other incident entrance 11 side. This also applies to the emitter 13.

In the present modified example, for example, suppose one of the light sources 101 emits the first primary light, and another light source 101 emits a second primary light. The optical characteristics of the first primary light, such as the wavelength, is different from the optical characteristics of the second primary light. At the detector 50 arranged near each of the incident entrances 11, one of the detectors 50 may detect the first primary light, and the other may detect the second primary light. In this case, for example, a photo diode of the detector 50 comprises a filter which transmits only a light having a predetermined wavelength. In this manner, each of the detectors 50 is capable of selectively detecting the primary light, and the calculator 105 is capable of individually calculating the light intensity of the light emitted by the light source 101.

Third Embodiment (Configuration)

Figure 9:
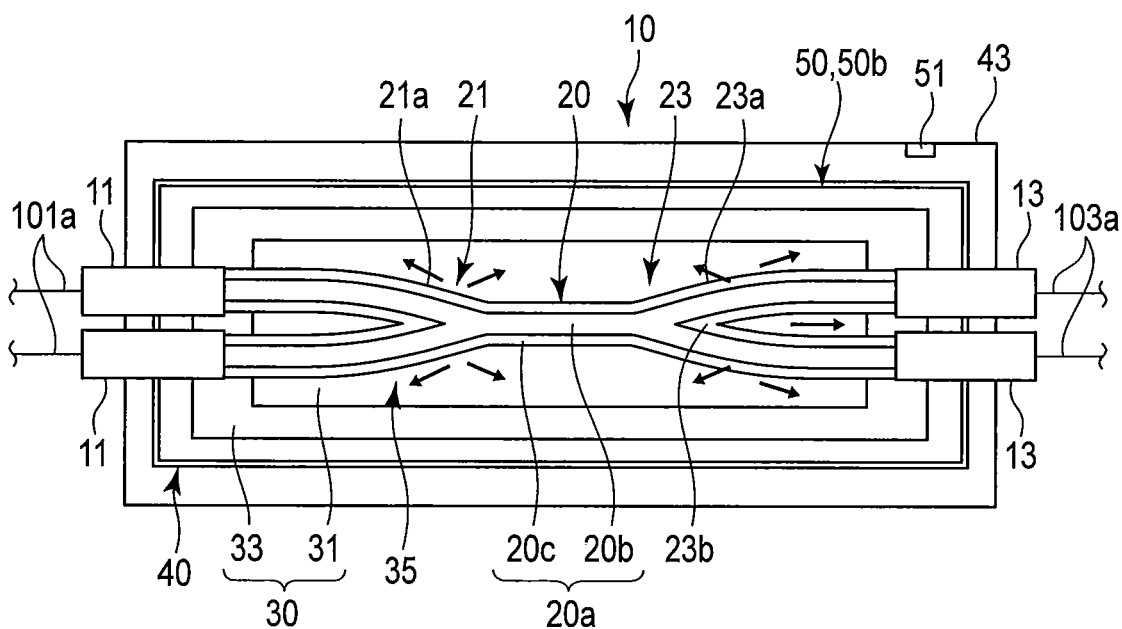
FIG. 9 is a diagram of an optical unit in a third embodiment viewed from above in a state where two incident entrances and two emitters are arranged.

With reference to FIG. 9, only a configuration different from that of the first embodiment will be explained below. Configurations similar to those described in the first embodiment will be denoted by the same reference symbols as used above, and a detailed description of such structures will be omitted.

The detector 50 comprises a heat converter (heat conversion member) 50b which is arranged, for example, on the entire surface of the inner periphery surface of the first exterior member 40. The heat converter 50b absorbs the primary light leaking out from the light coupler 21 and the light separator 23 and converts it into heat. By the heat converter 50b absorbing the primary light and converting it into heat, the detector 50 detects the change in heat, and indirectly detects the leakage light based on the change in heat.

The optical unit 10 further comprises a third exterior member 43 which is installed exterior to the incident entrance 11, the emitter 13, the optical element 20, the fixed substrate portion 30, and the first exterior member 40, and an outside air detector (outside air detection portion) 51 is arranged on at least one of the inner periphery surface and the outer periphery surface of the third exterior member 43, and detects the temperature of the outside air.

Prior to the optical unit 10 being actually used in a state where, for example, it is mounted on the endoscope 201 or the light source device 203, the calculator 105 calculates in advance the light intensity of the primary light emitted from the light source 101. The calculator 105 may acquire information regarding the light intensity of the primary light emitted from the light source 101 from the light source controller 209. The calculator 105 calculates the leakage light in advance based on the leakage light detected by the detector 50. The calculator 105 calculates in advance the correlation between the light intensity of the primary light emitted from the light source 101 and the leakage light.

(Advantages)

In the present embodiment, the third exterior member 43 is capable of preventing the outside light or the temperature of the outside air from affecting the temperature detection of the detector 50. In this manner, in the present embodiment, the detector 50 is capable of reliably detecting only the leakage light inside the first exterior member 40. In the present embodiment, the outside air detector 51 is also capable of detecting the temperature of the outside air.

The present embodiment is capable of detecting the light intensity of the primary light which is guided inside the optical element 20 based on the detection result detected by the detector 50, and the correlation between the light intensity of the primary light emitted from the light source 101 and the leakage light recorded in the recording unit 205a. In the present embodiment, the light intensity of the primary light guided inside the light converter 103 can be detected based on this detection result and the correlation between the light intensity of the emission light emitted from the light source 101 and the leakage light recorded in the recording unit 205a. The present invention is not limited exactly to the above-described embodiments, and can be provided by modifying the constituent elements without departing from the gist in the embodiment stages. By combining the plurality of constituent elements disclosed in the embodiments as appropriate, various inventions may be formed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical unit which comprises one or more incident entrances into which a primary light emitted from a light source enters, and one or more emitters from which the primary light entered from the incident entrance and guided by the optical unit is emitted, wherein at least one of the incident entrances and the emitters are arranged in a plurality of numbers, the optical unit comprising:

an optical element comprising the incident entrance, the emitter, a light coupler which is arranged in a case where a plurality of incident entrances are arranged, and which couples each of the primary lights entering from each of the incident entrances in a manner that each of the primary lights entering from each of the incident entrances is guided towards the emitter side, and a light separator which is arranged in a case where a plurality of emitters are arranged, and which separates the primary light towards each of the emitters in a manner that the primary light guided from the incident entrance side is further guided to each of the emitters, the optical element serving as a light guide path which guides the primary light from the incident entrance to the emitter via the light coupler and the light separator; and a detector which directly or indirectly detects a leakage light leaking outside of the light guide path from the light guide path, including the light coupler and the light separator between the incident entrance and the emitter, and which is arranged at a position away from the optical element.

2. The optical unit according to claim 1, wherein the detector is arranged in a range where the leakage light leaking out from at least one of a part of the light guide paths positioned between each of the incident entrances and the light coupler, the light coupler, the light separator, and a part of the light guide path positioned between the light separator and each of the emitters can reach the detector, and detects the leakage light.

3. The optical unit according to claim 2, wherein the detector comprises a detection member which directly detects a light intensity of the leakage light.

4. The optical unit according to claim 3, wherein at least one detector is arranged at least one of near the light coupler in a manner facing the light coupler in a height direction of the optical unit, and near the light separator in a manner facing the light separator in the height direction of the optical unit.

5. The optical unit according to claim 4, wherein the detector is arranged near the light coupler and near the light separator.

6. The optical unit according to claim 5, wherein the optical element further comprises a refractive index member which is arranged at a portion where the leakage light leaks out, and has a refractive index equal to or larger than a refractive index of an outermost layer of the optical element.

7. The optical unit according to claim 3, wherein, in a case where the detector is arranged near the light guide path positioned between each of the incident entrances and the light coupler, the detector is arranged near the light guide path positioned between one of the incident entrances and the light coupler, and near the light guide path positioned between the other incident entrance and the light coupler, and, in a case where the detector is arranged near the light guide path positioned between the light separator and each of the emitters, the detector is arranged near the light guide path positioned between the light separator and one of the emitters, and near the light guide path positioned between the light separator and the other emitter.

8. The optical unit according to claim 2, further comprising a first exterior member installed exterior to the optical element, wherein the detector comprises a heat converter which is arranged on an inner periphery surface of the first exterior member, and absorbs the leakage light and converts it into heat, and the detector detects the leakage light indirectly by the heat converter.

9. The optical unit according to claim 8, further comprising:

a second exterior member which is installed exterior to the first exterior member; and an outside air detector which is arranged on at least one of an inner periphery surface and an outer periphery surface of the second exterior member, and detects a temperature of an outside air.

10. The optical unit according to claim 1, wherein the optical element comprises an optical fiber, and serves as an optical fiber coupler formed by the light coupler and the light separator, and the optical fiber comprises a core and a cladding having a refractive index lower than that of the core and covering an outer periphery surface of the core.

11. An endoscope system, comprising:

a light source which emits a primary light;

an optical unit according to claim 1;

a light converter which performs light conversion on the primary light emitted from the emitter and which emits the light converted primary light outside; and a calculator which calculates a light intensity on the light guide path based on the leakage light detected by the detector of the optical unit.

12. The endoscope system according to claim 11, wherein the optical unit is arranged on one of a distal end portion of an insertion portion of an endoscope, and a light source device is connected to the endoscope and comprises the light source.

13. The endoscope system according to claim 12, wherein, in a case where the detector is arranged near the light coupler and near the light separator, the calculator calculates a difference between a detection result of the detector at the light coupler and a detection result of the detector at the light separator.

* * * * *